United States Patent [19]

Holmes

[11] 4,239,038
[45] Dec. 16, 1980

[54] MANUAL RESUSCITATORS

[75] Inventor: Ronald W. Holmes, Ringwood East, Australia

[73] Assignee: The Commonwealth Industrial Gases Limited, Australia

[21] Appl. No.: 18,082

[22] Filed: Mar. 6, 1979

[30] Foreign Application Priority Data

Mar. 7, 1978 [AU] Australia .............................. 3620/78

[51] Int. Cl.³ ............................................ A61M 16/00
[52] U.S. Cl. .......................... 128/205.13; 128/205.24; 137/102; 137/DIG. 9; 137/512.4
[58] Field of Search ............... 128/145.7, 145.8, 145.6, 128/188, 205.24, 205.13, 207.12; 137/102, DIG. 9, 512.4

[56] References Cited

U.S. PATENT DOCUMENTS

| 3,460,558 | 8/1969 | Johannisson | 137/102 |
| 3,556,122 | 1/1971 | Laerdal | 137/102 |

FOREIGN PATENT DOCUMENTS

| 2424798 | 11/1975 | Fed. Rep. of Germany | 128/145.8 |
| 2320118 | 3/1977 | France | 128/145.7 |
| 362603 | 7/1962 | Switzerland | 137/DIG. 9 |
| 910065 | 11/1962 | United Kingdom | 128/145.7 |

Primary Examiner—Henry J. Recla
Attorney, Agent, or Firm—Beveridge, DeGrandi, Kline & Lunsford

[57] ABSTRACT

A manually operable resuscitator includes a manually deflatable gas reservoir to supply gas to a hollow valve housing for controlled supply to and from a patient. The housing has three ports, a first one for connection to the reservoir, a second one for supply to the patient and a third one for exhaust to atmosphere. A distensable diaphragm which is distended by pressure in the reservoir to open the first port and close the third port. A non-return valve controls flow from the first port to the second port. The diaphragm may carry a valve to permit flow from the first to the second port if pressure drops in the latter as the patient inhales.

6 Claims, 8 Drawing Figures

MANUAL RESUSCITATORS

BACKGROUND OF THE INVENTION

This invention relates to manually operated resuscitators of the kind used to assist or re-establish the breathing of a patient when that function has become impaired or has failed as a result of immersion, electric shock, or other accidental circumstance or illness detrimental to the normal breathing capability.

Such resuscitators conventionally comprise a recoilable self-inflating bag type reservoir into which breathable gas is drawn and from which the said gas may be directed to a patient, a valve assembly for directing a flow of breathable gas to the patient and exhaled gas from the patient to atmosphere, to which assembly is attached a face mask or endotracheal tube which in use is applied to the patient in known manner.

Improvements to manually operated resuscitators include supplemental oxygen supply to enrich the atmospheric air drawn into the reservoir during recoil which provides a low concentration of oxygen mixture, e.g. 50% oxygen in air.

Nevertheless an undesirable feature of such manually operated resuscitators is the rebreathable gas space which exists following patient exhalation when such exhalation gas is permitted to re-enter the reservoir during the period of recoil and inflation thereof. This reduces the amount of oxygen available to the patient during subsequent inhalation steps and permits exhaled carbon dioxide to be delivered back to the patient, which is considered to be detrimental to the patient.

A further undesirable feature exists in the multiplicity of component parts which generally are used in the assembly of the gas valve or valves. In such cases risk exists that a particular component may be misassembled or may even be omitted from the assembly. Such a complicated or multiple assembly as has been used requires a comparatively large occupant space which can at times become unwieldly in use and also tends to provide a too large capacity space for inhaled gas retention.

SUMMARY OF THE INVENTION

With the foregoing in mind the present invention has been devised to provide a valve assembly for such a respirator in which exhaled gas is prevented from returning to the reservoir and the space in which the exhaled gas is retained is kept small, thus ensuring that the subsequent inhalation gases to the patient include only a small proportion of carbon dioxide.

The invention consists in a resuscitator valve assembly comprising:

a hollow valve housing defining an inlet port adapted to be connected to a self-expanding manually deflatable reservoir of breathable gas, an intermediate port adapted to be connected to patient supply means, and an exhaust port; a deformable closure diaphragm normally closing the inlet port and allowing communication between the intermediate port and the exhaust port but able to be distended by pressure within the inlet port to a position wherein it opens the inlet port and closes the exhaust port; and a normally closed non-rebreathing valve which is exposed to the inlet port when, and only when, the diaphragm is distended and which then permits gas flow from the inlet port to the intermediate port but prevents flow in the opposite direction.

BRIEF DESCRIPTION OF THE DRAWINGS

By way of example, preferred embodiments of the above described invention are described hereinafter with reference to the accompanying drawings.

In those drawings.

DESCRIPTION OF THE PREFERRED EMBODIMENTS

Figure 1:
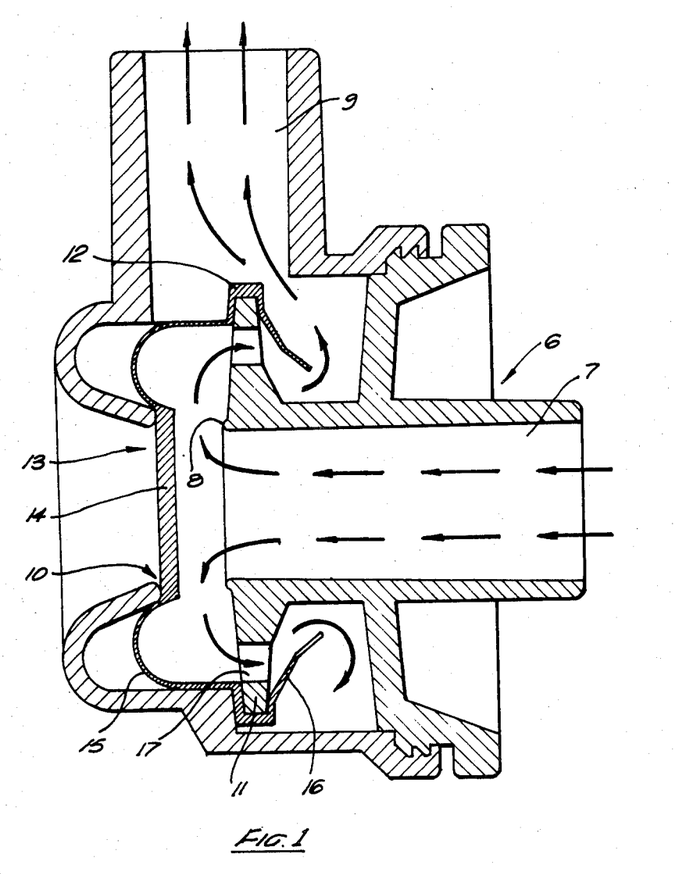
FIG. 1 is a sectional view of a valve arrangement according to the invention showing the arrangement in the position it adopts when the patient is inhaling breathable gas delivered under pressure from the reservoir (inflation mode).

The embodiment of the invention illustrated by FIG. 1 comprises a two-part valve housing comprising a first component 6 including an inlet port in the form of a spigot 7 adapted to be connected to a reservoir of breathable gas and defining an inlet valve seat 8 and a second component defining an intermediate port in the form of a spigot 9 adapted to be connected to a face mask, mouth piece or other patient supply means for communicating with the lungs of a patient, and defining an exhaust valve seat 10 rimming an exhaust port.

The first component 6 includes an outwardly directed peripheral end flange 11 able to be embraced by a circumferential channel sectioned portion 12 of an elastomeric, gas impervious closure diaphragm 13.

The diaphragm 13 comprises, as well as the channel sectioned peripheral portion 12, a closure disc 14 connected by pliable annular membrane 15 to the channel sectioned peripheral portion 12 and an annular, radially inwardly directed peripheral skirt 16.

The flange 11 has a plurality of openings 17 extending through it which openings are adapted to be closed by contact of the skirt 16 with the adjacent face of the flange 11. Thus the flange 11 and skirt 16 constitute a non-return valve referred to as a non-rebreathing valve herein.

When the patient is forced to inhale, gas from the reservoir flows under pressure and the pressure differential between the lungs of the patient and the reservoir causes the diaphragm 13 to distend and the flap 16 to lift away from flange 11 to permit gas to flow as indicated by the arrows in FIG. 1. At the same time the distention of the diaphragm brings the valve disc 14 into the position shown in FIG. 1 to seal against the exhaust valve seat 10.

On completion of such forced "inhalation" the reservoir is allowed to recoil thus inflating with breathable gas for a subsequent inhalation phase. The diaphragm reasserts itself so that closure disc 14 comes back into contact with the inlet valve seat 8 and skirt 16 closes off opening(s) 17. Exhalation by the patient assists the aforesaid reassertion by the diaphragm and the exhaled gas is exhausted to atmosphere via the exhalation port which is encircled by the exhalation valve seat 10.

Thus it will be seen that movement of the disc 14 coinciding with movement of the skirt 16 and also coinciding with the inhalation and exhalation of the patient permits gas from the reservoir to flow under pressure to the patient and exhaled gas to flow from the patient to atmosphere with almost no inhalation by the patient of previously exhaled gas.

Figure 2:
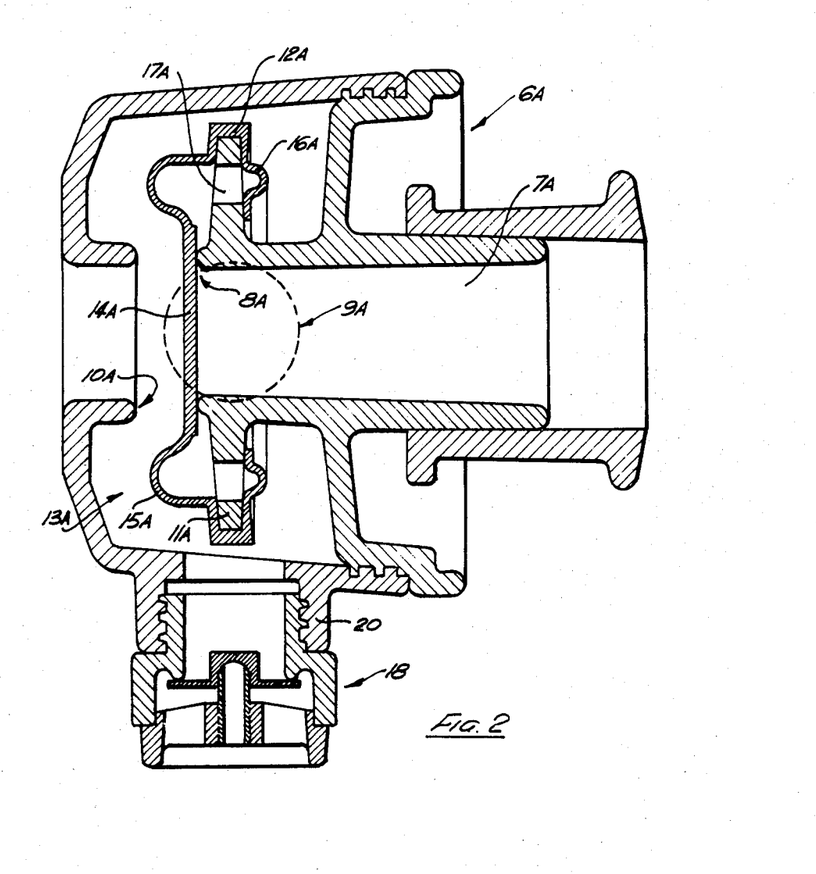
FIG. 2 is a view similar to FIG. 1 of a valve arrangement according to a second embodiment of the invention showing the position it adopts when the patient is exhaling (expiration mode).

The valve assembly illustrated by FIG. 2 is similar in its functional capabilities and in many of its components to the assembly of FIG. 1 and need not be described in detail insofar as it corresponds to FIG. 1.

The various components of the assembly of FIG. 2 which correspond directly to those of FIG. 1 are not therefore further described herein but their reference numerals in FIG. 2 correspond to those of FIG. 1 but with the suffix "A" appearing thereafter.

Figure 4:
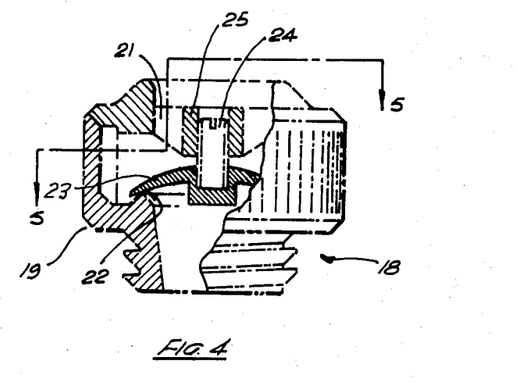
FIG. 4 is a partly sectioned elevation of a relief valve being an optional component of the valve arrangement of FIG. 2
Figure 5:
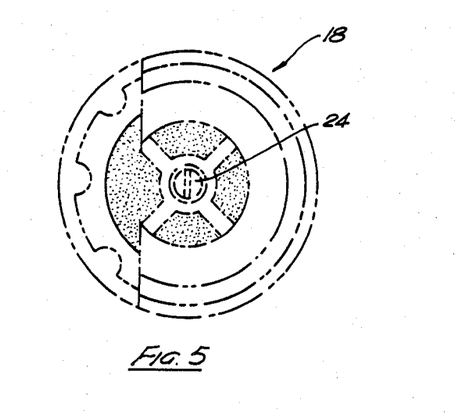
FIG. 5 is a sectional view taken on line 5—5 of FIG. 4.

The main difference between the FIG. 2 embodiment and the FIG. 1 embodiment of the invention is the presence in the FIG. 2 embodiment of a relief valve assembly 18 illustrated in more detail in FIGS. 4 and 5.

The relief valve assembly 18 comprises a relief valve casing 19 able to be screwed into a socket 20 on the second component of the main valve assembly and defining outlet vents 21, a relief valve seat 22 and a resilient relief valve closure element 23. The Force with which the relief valve closure elements 23 bears upon the seat 22 may be adjusted by means of an adjuster screw 24 carrying the element 23 and able to be moved axially by rotational movement in an internally threaded bush 25 towards or away from the seat 22.

The purpose of the relief valve assembly 18 is to ensure that if the reservoir containing breathable gas is too forcibly compressed by an operator so as to possibly overpressurize the lungs of a patient this will be counteracted by the valve element 23 moving resiliently away from the seat 22 and relieving the excess pressure. Clearly other forms of relief valve could be used if desired.

Figure 3:
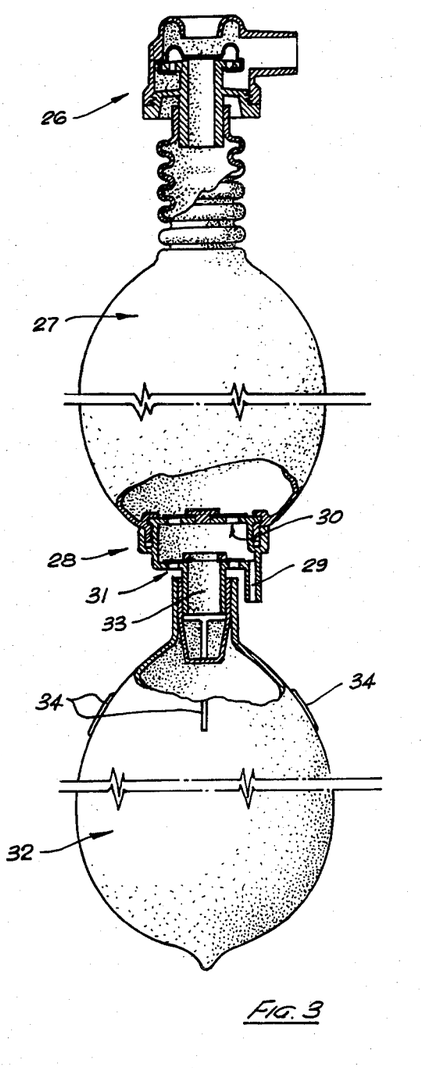
FIG. 3 is a sectional view of a resuscitator incorporating a valve arrangement according to FIG. 2.

FIG. 3 illustrates a complete resuscitator including a valve assembly 26 identical with the assembly of FIGS. 2, 4 and 5. That assembly is connected to a reservoir 27 which is provided with a gas inlet assembly 28.

The gas inlet assembly 28 includes a spout 29 adapted to receive a pipe connection from a regulated pressure source of breathable gas. It also includes a non-return diaphragm type valve 30 and a non-return diaphragm type valve 31. The purposes of the valves 30 and 31 are to ensure that gas flowing from the gas source may enter the reservoir 27 through valve 30 and thereafter cannot be expelled otherwise than through the valve assembly 26 to the patient. On the other hand if there should be a failure of the supply of gas from the source due, for example, to exhaustion of the available gas in that source, then atmospheric air may still be delivered to the patient such air being drawn into the reservoir 27, after its manual compression, by its natural tendancy to return to its distended position, through the valve 31.

A reserve bladder 32 is also attached to the assembly 28 and there is an unobstructed large diameter passageway 33 connecting the interior of bladder 32 to the interior of reservoir 27 via the valve 30. The purpose of the reserve bladder 32 is to provide a reserve of breathable gas for the replenishment of reservoir 27 upon its return to the distended condition, after it has been compressed to force breathable gas to the patient, at a sufficient rate to meet the patient's requirements should supply from the gas source through nozzle 29 be momentarily insufficient. Once the bladder 32 has been deflated in that way there is time for it to be refilled via the spout 29 from the main gas source whilst the reservoir 27 is being next compressed.

The bladder 32 may be fabricated from a plurality, say four, segments seam welded together and small gaps 34 in the continuity of the welds may be provided to prevent the bladder becoming overpressurized due to the continuous flow of gas from the main source via the spout 29 at times of low demand for gas by the patient.

Figure 6:
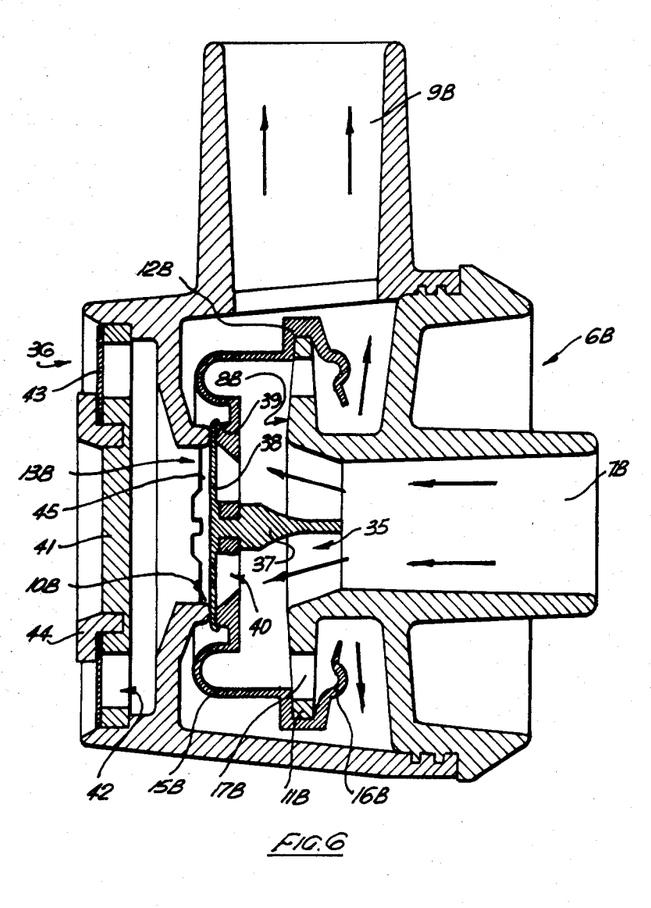
FIG. 6 is a view similar to FIG. 1 of a third embodiment of the invention shown in the inflation mode.
Figure 7:
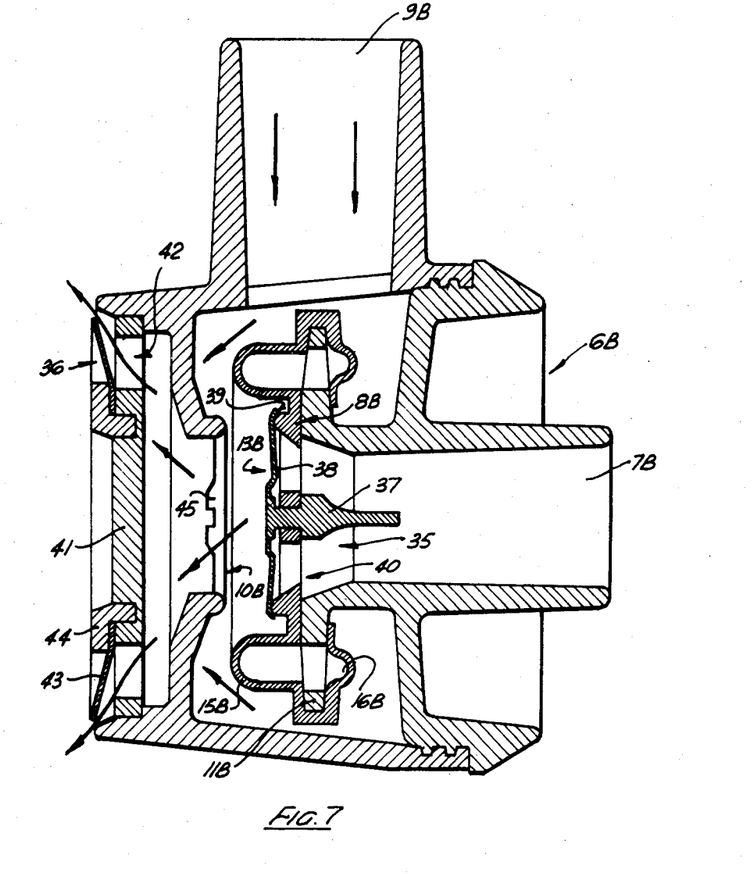
FIG. 7 is a view similar to FIG. 6 showing the arrangement of that Figure in its expiration mode.
Figure 8:
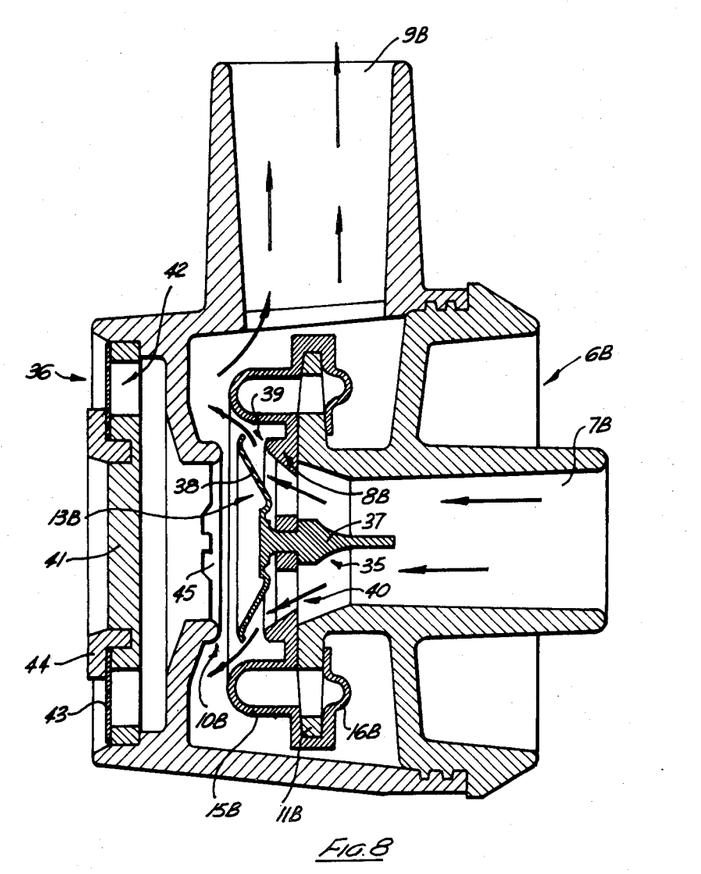
FIG. 8 is a view similar to FIG. 6 showing the arrangement of that Figure in the inhalation mode.

The embodiment of the invention illustrated by FIGS. 6–8 is similar in its functional capabilities and in many of its components to the assembly of FIG. 1 and need not be described in detail insofar as it corresponds to FIG. 1.

The various components of the assembly of FIGS. 6–8 which correspond directly to those of FIG. 1 are not therefore further described herein but their reference numerals in FIGS. 6–8 correspond to those of FIG. 1 but with the suffix "B" appearing thereafter.

The differences between the assembly now being described and that of FIG. 1 is the replacement of disc 14 of the latter by a tandem valve 35 and the inclusion of a non-return outlet valve 36.

The tandem valve 35 comprises a mushroom type valve element comprising a stem 37 and a pliable skirt 38. The stem 37 is retained gas-tightly in a central hole in the diaphragm 13B and the skirt 38 is adapted to close against the exhaust valve seat 10B (FIG. 6) and against a rim seat 39 on the diaphragm 13B encircling a plurality of openings 40 therethrough. A cross-shaped spider 45 may span the opening rimmed by seat 10B to help support the skirt 38 when closed against that seat.

The valve 36 comprises a rigid sealing disc 41 which would block the outlet of the assembly except for a circular array of holes 42 extending through it and a pliable annular valve element 43 secured to the disc 41 by clamping ring 44 and adapted to cover the holes 42.

The purpose of the tandem valve 35 and non-return valve 36 is to enable the resuscitator to be used when the patient is in a poisonous or other non-breathable ambient atmosphere. While the patient is not breathing spontaneously the pressures are determined by the forced compression and recoil of the reservoir and the arrangement functions much as for the earlier described embodiments with the tandem valve element moving as one with the central portion of the diaphragm and the non-return valve opening as needed to allow the patient to exhale but otherwise not playing any useful function.

However once the patient commences to breathe spontaneously he is likely to inhale perhaps while the reservoir is expanding. In that event he could, in the absence of the non-return valve, draw in poisonous ambient atmosphere but with this arrangement that is avoided as the non-return valve closes and the tandem valve opens to exclude the ambient atmosphere and allow breathable gas to be drawn from the reservoir. In such instances the valve 31 is omitted thus the patient inhales breathable atmosphere through valve 35 and exhales through non-return valve 36.

I claim:

1. A resuscitator valve assembly comprising a hollow valve housing defining an inlet port adapted to be connected to a self-expanding manually deflatable reservoir of breathable gas, an intermediate port adapted to be connected to patient supply means, and an exhaust port opposite said inlet port; a tubular section having a first end defining said inlet port and a second end projecting internally of said housing from said inlet port and spaced from said exhaust port and terminating in an annular valve seat, said second end further including an annular flange projecting radially therefrom; a deformable closure diaphragm overlying said valve seat and said flange and having a peripheral radially inwardly directed, channel-sectioned portion, the rim of the flange being secured within said channel-sectioned portion, said deformable closure diaphragm normally positioned on said valve seat and allowing communication between the intermediate port and the exhaust port but able to be distended by pressure at the inlet port to a position away from said valve seat it opens the inlet port and closes the exhaust port; and non-rebreathing valve means comprising at least one hole defined in said flange intermediate said rim and said tubular section second end and extending through said flange, and an annular resilient skirt projecting radially inwardly from the channel-sectioned portion of the diaphragm whereby said at least one hole is normally closed by said skirt, said non-rebreathing valve means being exposed to the inlet port when, and only when, the diaphragm is distended thereby to permit gas flow from the inlet port to the intermediate port but preventing flow in the opposite direction.

2. A valve assembly according to claim 1 wherein said valve housing is provided with a pressure relief valve.

3. A valve assembly according to claim 1 wherein the central portion of the diaphragm carries a tandem valve which opens in consequence of sub-atmospheric pressure in said intermediate port to permit gas flow from the inlet port to the intermediate port when the diaphragm is not distended and including non-return valve means mounted in said exhaust port to close the exhaust port thereby preventing flow from ambient atmosphere into said housing through said exhaust port in response to said subatmospheric pressure in the intermediate port.

4. A resuscitator comprising a valve assembly according to claim 3, a self-expanding, manually deflatable reservoir connected to said inlet port, a reserve bladder connected to the reservoir by means of a passageway, means to supply a breathable gas to said reservoir and said bladder from a pressurised source of gas and reservoir non-return valve means mounted in said passageway to prevent flow from said reservoir into said bladder.

5. A resuscitator comprising a valve assembly according to claim 1, a self-expanding, manually deflatable reservoir connected to said inlet port, a reserve bladder connected to the reservoir by means of a passageway, means to supply a breathable gas to said reservoir and said bladder from a pressurized source of gas, reservoir non-return valve means mounted in said passageway to prevent flow from said reservoir into said bladder during manual deflation of said reservoir, and an air inlet having non-return valve means mounted in said passageway responsive to pressure in said bladder and to permit ambient air to enter said reservoir when the supply of breathable gas from said bladder is exhausted.

6. A resuscitator according to either claims 4 or 5 wherein said bladder has a pressure relief vent.

* * * * *